(12) United States Patent
Hatakeyama

(10) Patent No.: US 9,592,835 B2
(45) Date of Patent: Mar. 14, 2017

(54) SLEEPINESS DETECTING DEVICE

(71) Applicant: TOYOTA JIDOSHA KABUSHIKI KAISHA, Toyota-shi (JP)

(72) Inventor: Yoshiyuki Hatakeyama, Fuji (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 0 days.

(21) Appl. No.: 15/085,121

(22) Filed: Mar. 30, 2016

(65) Prior Publication Data

US 2016/0304099 A1    Oct. 20, 2016

(30) Foreign Application Priority Data

Apr. 18, 2015  (JP) .................................. 2015-085497

(51) Int. Cl.
*B60W 40/08* (2012.01)
*A61B 5/11* (2006.01)
(Continued)

(52) U.S. Cl.
CPC ............... *B60W 40/08* (2013.01); *A61B 3/14* (2013.01); *A61B 5/0496* (2013.01);
(Continued)

(58) Field of Classification Search
CPC . B60W 40/08; B60W 2040/0827; A61B 3/14; A61B 5/0496; A61B 5/1103; A61B 5/18; A61B 5/6893; A61B 5/7282
(Continued)

(56) References Cited

U.S. PATENT DOCUMENTS

2009/0027212 A1  1/2009 Nakagoshi et al.
2011/0313259 A1  12/2011 Hatakeyama et al.
(Continued)

FOREIGN PATENT DOCUMENTS

JP    2007-236488    9/2007
JP    2011-167398    9/2011

OTHER PUBLICATIONS

Hiroki Kitajima, et al., Prediction of Automobile Driver Sleepiness ($1^{st}$ Report, Rating of Sleepiness Based on Facial Expression and Examination of Effective Predictor Indexes of Sleepiness), Bulletin of JSME (C series) vol. 63 No. 613 (Sep. 1997) Paper No. 96-1780, pp. 3059-3066 (with English abstract).

*Primary Examiner* — McDieunel Marc
*Assistant Examiner* — James E Stroud
(74) *Attorney, Agent, or Firm* — Oblon, McClelland, Maier & Neustadt, L.L.P.

(57) ABSTRACT

A device for detecting the sleepiness of a driver driving a vehicle is designed to determine if the resetting of threshold values for detection of sleepiness is performed based upon its necessity when an interruption of the driving occurs. The inventive device computes successively an eyelid opening/closing characteristic amount from time intervals between transitions between an opened state and a closed state of an eyelid detected successively; sets threshold values using the eyelid opening/closing characteristic amounts obtained in a predetermined period; and judges the driver feels sleepiness when the eyelid opening/closing characteristic amount deviates from a range defined with the threshold values. In restarting the driving after its interruption, it is judged if the resetting of the threshold values is to be performed based on the driver's condition till then, and the resetting is performed, using eyelid opening/closing characteristic amounts obtained after the restarting of the driving.

12 Claims, 8 Drawing Sheets

Figure 1A:
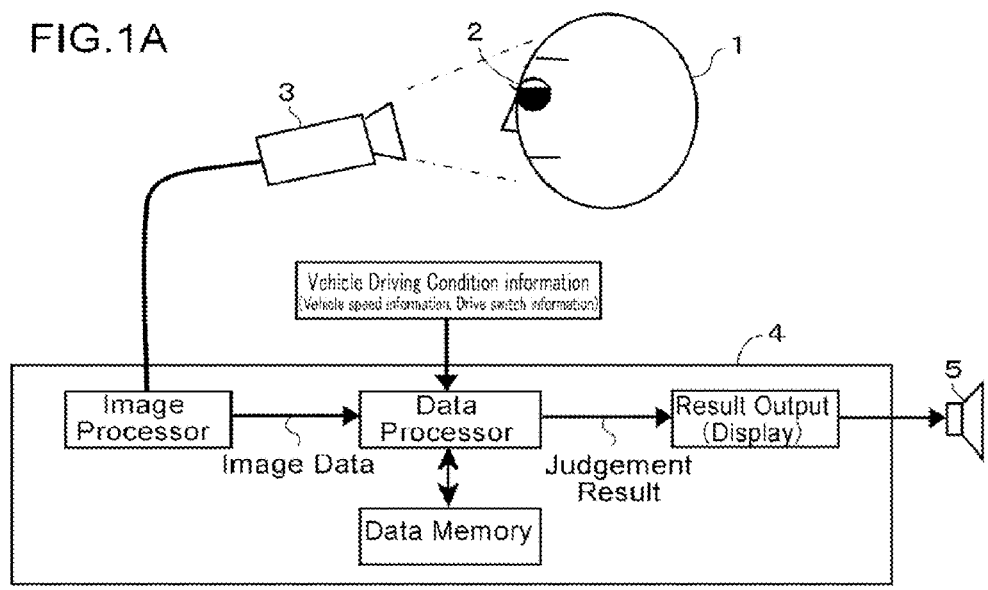

(51) Int. Cl.
*A61B 5/18* (2006.01)
*A61B 3/14* (2006.01)
*A61B 5/0496* (2006.01)
*A61B 5/00* (2006.01)

(52) U.S. Cl.
CPC .............. *A61B 5/1103* (2013.01); *A61B 5/18* (2013.01); *A61B 5/6893* (2013.01); *A61B 5/7282* (2013.01); *B60W 2040/0827* (2013.01)

(58) Field of Classification Search
USPC ........................................................... 701/1
See application file for complete search history.

(56) References Cited

U.S. PATENT DOCUMENTS

| | | | | |
|---|---|---|---|---|
| 2012/0212353 | A1* | 8/2012 | Fung | B60K 28/06 340/905 |
| 2015/0003126 | A1* | 1/2015 | Kim | H02M 1/32 363/50 |
| 2015/0104081 | A1* | 4/2015 | Ionita | G06K 9/4614 382/117 |
| 2016/0140390 | A1* | 5/2016 | Ghosh | G06K 9/00597 348/78 |
| 2016/0167672 | A1* | 6/2016 | Krueger | A61M 21/00 340/576 |
| 2016/0171321 | A1* | 6/2016 | Ohsuga | G06K 9/00845 345/419 |
| 2016/0185354 | A1* | 6/2016 | Lisseman | B62D 1/046 701/36 |
| 2016/0198968 | A1* | 7/2016 | Plenz | A61B 5/04001 600/544 |
| 2016/0235343 | A1* | 8/2016 | Hatakeyama | A61B 5/1103 |

* cited by examiner

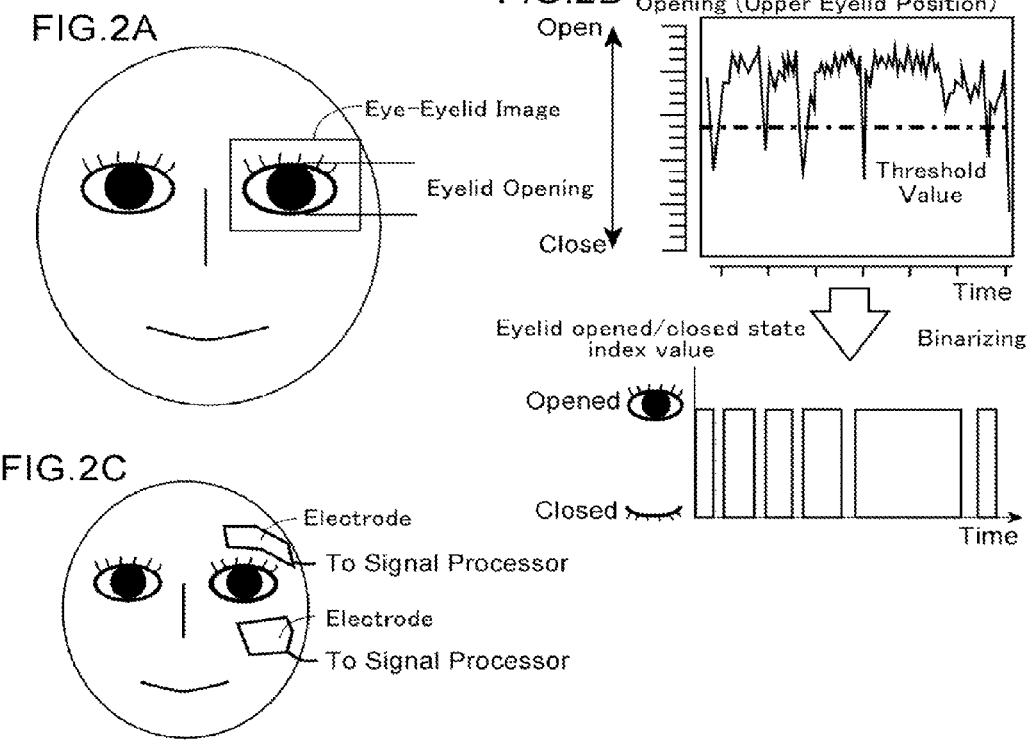

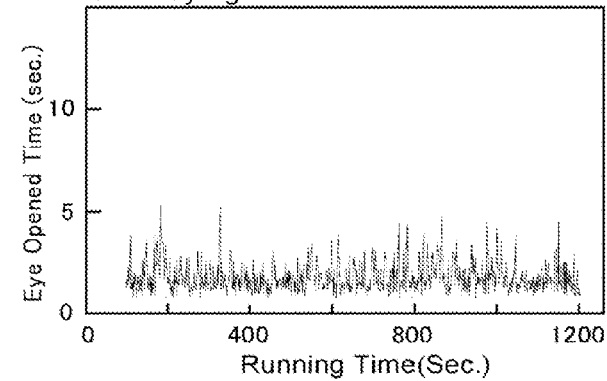
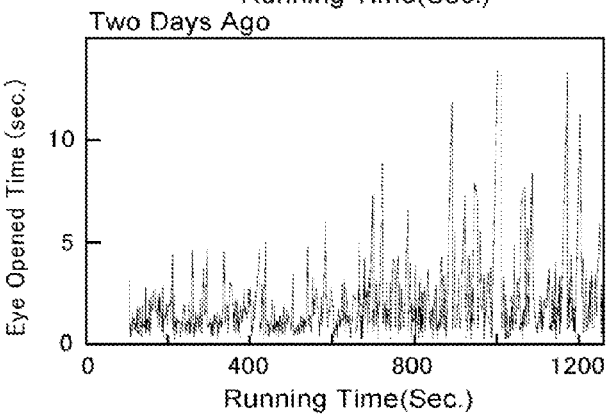
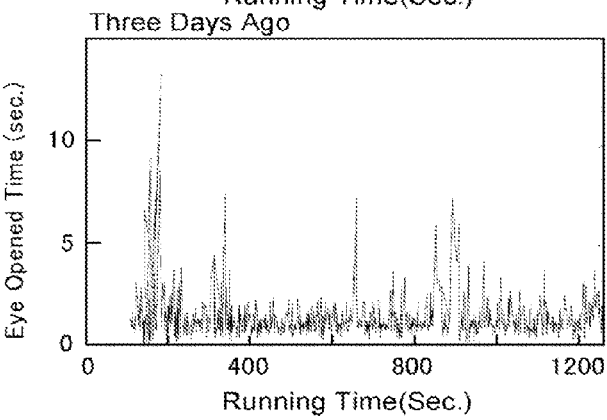
FIG. 8
One Day Ago
Two Days Ago
Three Days Ago
Extracting Data During Running on an Ordinary Road
$$Mav = \frac{\sum_i SD(ti)}{N_{1d.+2d.+3d.}}$$
Used For Setting Threshold values

SLEEPINESS DETECTING DEVICE

TECHNICAL FIELD

This invention relates to a device which detects sleepiness of a human being, and more specifically to a device which detects an occurrence of sleepiness based on an index value obtained from the opening and closing motions of an eyelid of a human being. This inventive device can be used for detecting the sleepiness of a driver during driving a vehicle or a mobile body.

BACKGROUND ART

As a device which detects sleepiness of a human being, there have been proposed a variety of devices judging if a person feels sleepiness by capturing an image of a face or an eyelid of the person and catching a motion of the eyelid and/or other variations in the facial expression in the captured image. For instance, patent document 1 proposes a structure, in which the length of a time in which an eyelid is continuously opened (hereafter, referred to as "eye opened time") is measured in captured images of an eye and its circumferential area of a subject being tested; the dispersion in the eye opened time (the standard deviation) is computed; and when the standard deviation of the eye opened time falls below a predetermined threshold value together with an increase in sleepiness, "a nap occurred" is judged. Further, in patent document 2, there has been proposed a structure in which occurrences of four sorts of facial expressions, including mouth motions in sighing, yawning, opening eyes widely and frowning, are measured from images of a subject's face, and an awakening degree, defined corresponding to an occurrence frequency of a combination of two of different sorts of the facial expressions, is outputted as an estimated result.

PRIOR TECHNICAL DOCUMENTS

Patent Documents

Patent document 1; JP2011-167398
Patent document 2: JP2007-236488

Non-Patent Documents

Non-Patent document 1: Bulletin of JSME (C series) Vol. 63 No. 613 (1997-9) Paper No. 96-1780, pages 3059-3066

SUMMARY OF INVENTION

Technical Problem

With respect to sleepiness detecting devices as described above, there occurs a case that the standard deviation of the eye opened time increases, depending upon subjects, because some subjects blink violently or open eyes wide intentionally in order to prevent eyelids from closing together with the increase of sleepiness. Thus, in order to make it possible to detect an occurrence of sleepiness of a subject with accuracy more sufficient than before even in a case of a subject who intentionally blinks more violently, opens eyes wider or makes opening and closing motions of eyes more vigorous than usual in order to prevent from closing eyelids, instead of the opening and closing movement of eyelids being slow, in the increase of the sleepiness, the inventor of the present invention has proposed a structure of judging that a subject feels sleepiness when an "eyelid opening/closing characteristic amount", which is a quantity having a correlation with the presence or absence or the degree of the sleepiness of a subject, deviates from a range defined with the upper and lower threshold values where the subject does not feel sleepiness (Japanese Patent Application No. 2015-25886).

By the way, in the above-mentioned sleepiness detecting device, the threshold values for the "eyelid opening/closing characteristic amount" are set based on eyelid opening/closing characteristic amounts measured in a condition that a subject does not feel sleepiness (referred to as a "normal condition" in the followings). In this respect, even in the normal condition, there occur individual variations and intraindividual variations (variations owing to a situation change around the subject) in the eyelid opening/closing characteristic amount. Also, there are scatterings at a certain degree in actual measurement values of the eyelid opening/closing characteristic amount. Thus, in detecting sleepiness for a certain subject, it is preferable to determine the threshold values for the "eyelid opening/closing characteristic amount" by using "eyelid opening/closing characteristic amounts", measured for a period until statistically significant data volume can be obtained, in a term relatively close to a time of performing the detection of the sleepiness while the subject is in normal condition. So, in a case that the sleepiness detecting device is used for detecting sleepiness of a driver during driving a vehicle, such as an automobile, typically, the threshold values for the "eyelid opening/closing characteristic amount" are set based upon eyelid opening/closing characteristic amounts of the driver in a predetermined period just after the starting of the driving.

With respect to a case of using the sleepiness detecting device for detecting sleepiness of a driver during driving a vehicle as noted above, the driving of the vehicle is often performed with an interruption, such as taking a break (a rest), etc., and depending upon the manner of the interruption (the way of spending time, the length of a break, etc.), the condition of the driver in restarting the driving may change from the condition before the interruption. Then, if the eyelid opening/closing characteristic amount in the normal condition has changed from the condition before the interruption, an erroneous decision of sleepiness (an erroneous detection, the overlooking of an occurrence of sleepiness) may be caused in the judgment process of sleepiness with the threshold values set based on the normal condition before the interruption. Thus, in order to perform the detection of sleepiness during driving a vehicle with more sufficient accuracy, it is preferable to repeat the re-setting of threshold values for the "eyelid opening/closing characteristic amount" after every interruption of the driving of a vehicle. However, as noted above, the setting of the threshold values for the "eyelid opening/closing characteristic amount" takes a predetermined time period before actually performing the process of detecting sleepiness, and during this period, the detection of sleepiness could not be performed. Further, for example, when an interruption of the driving is relatively short, the condition of a driver rarely changes during the interruption, and in that case, the resetting of threshold values for the "eyelid opening/closing characteristic amount" after restarting the driving is unnecessary, and also, the detection of sleepiness of a driver will not be performed in the predetermined period for the resetting of threshold values in spite of its unnecessity. Thus, in a case that the sleepiness detecting device is used for the detection of sleepiness of a driver during driving a vehicle, it is preferable to determine or judge whether or not the resetting of threshold values for the "eyelid opening/closing characteristic amount" is to be performed after an interruption of the driving through estimating the necessity for the resetting of threshold values based on a change of the condition of the driver before and after the interruption of the driving, etc.

Thus, one object of the present invention is to provide a sleepiness detecting device for detecting sleepiness of a driver during driving a vehicle, having a structure of determining whether to perform the resetting of threshold values for the "eyelid opening/closing characteristic amount" used for detecting sleepiness (judgment of the presence or absence of sleepiness) while taking into account the necessity for the resetting of threshold values.

Solution to Problem

According to the present invention, the above-mentioned object is achieved by a device for detecting sleepiness of a subject driving a vehicle (hereinafter, referred to as the "sleepiness detecting device"), comprising: an eyelid state detector which detects an opened/closed state of an eyelid of the subject, namely a driver; a time interval detector which detects sequentially a time interval between transitions between an opened state and a closed state of the eyelid; an eyelid opening/closing characteristic amount computer which computes an eyelid opening/closing characteristic amount successively from time series data of the time intervals between transitions between an opened state and a closed state of the eyelid; a threshold value setter which sets threshold values for the eyelid opening/closing characteristic amount using eyelid opening/closing characteristic amounts obtained in a predetermined period; and a sleepiness judging device for judging that the subject feels sleepiness when the eyelid opening/closing characteristic amount deviates from a range defined with the threshold values after lapse of the predetermined period; wherein the threshold value setter judges whether or not the threshold values is to be reset based on a condition of the subject before the restarting of the driving in restarting the driving of the vehicle after an interruption of the driving of the vehicle, and resets the threshold values for the eyelid opening/closing characteristic amount using eyelid opening/closing characteristic amounts obtained in a predetermined period after the restarting of the driving when it is judged that the threshold values are to be reset.

In the above-mentioned structure, the "eyelid state detector" may be an arbitrary device which can judge whether an eyelid of a subject is opened or closed, and typically, there may be employed a device which judges the opened/closed state of an eyelid based on an image of the subject's eyelid captured (photographed) by a camera. Alternatively, the "eyelid state detector" may be a device which judges the opened/closed state of an eyelid based on an ocular potential signal of the subject. The "time interval between transitions between an opened state and a closed state of the eyelid" is an interval between time points at which a transition in an eyelid from an opened state to a closed state or from a closed state to an opened state occurs in the data of judgment results of whether the eyelid is opened or closed obtained in time series by the "eyelid state detector". Concretely, this time interval may be: (1) a time interval from a transition of an eyelid from its closed state to its opened state to a transition of the eyelid from its opened state to its closed state, namely, a time length in which the eyelid is continuously opened (eye opened time); (2) a time interval from a transition of an eyelid from its opened state to its closed state to the next transition from its opened state to its closed state, namely, a time length from when an eyelid is closed until it is closed again after it is once opened (a blink start time interval); (3) a time interval from a transition of an eyelid from its closed state to its opened state to the next transition from its closed state to its opened state, namely, a time length from when an eyelid is opened until it is opened again after it is once closed (a blink end time interval); or (4) a time interval from a transition of an eyelid from its opened state to its closed state to a transition of the eyelid from its closed state to its opened state, namely, a time length in which the eyelid is continuously closed (eye closed time).

The "eyelid opening/closing characteristic amount" is, briefly speaking, an amount which correlates with the presence or absence, or the degree, of sleepiness of the subject, extracted from the above-mentioned "time interval between transitions between the opened state and closed state of an eyelid". Concretely, when a subject feels sleepiness, the "time interval between transitions between the opened state and closed state of an eyelid" statistically changes in comparison with when the subject does not feel sleepiness, and thus, for such a "eyelid opening/closing characteristic amount", there may be employed, for example, an index value indicating a statistical amount of the "time interval between transitions between the opened state and closed state of an eyelid", and more specifically, an standard deviation, an average value, a median value, variance value, etc., thereof may be employed. Especially, when a subject feels sleepiness, the opening and closing motions of the eyelid become slower or more vigorous than in usual conditions in the absence of sleepiness, so that its statistical variation will change. Thus, in that case, the standard deviation or variance value of the "time interval between the transition between the opened state and closed state of an eyelid" can be preferably employed for the "eyelid opening/closing characteristic amount". And, when the eyelid opening/closing characteristic amount deviates from a normal condition, namely, the range where the value of the amount can take in a condition that the subject does not feel sleepiness, it is judged that the subject feels sleepiness. The range that the value of the eyelid opening/closing characteristic amount can take in the normal condition is defined with eyelid opening/closing characteristic amounts obtained in a predetermined period in the threshold value setter. In this regard, as already noted, when a human being feels sleepiness, the change owing to this appears in the opening and closing motion of an eyelid, and typically, in many cases, the motion of the eyelid becomes slower so that the values and variation of the "time interval between transitions between the opened state and the closed state of the eyelid" will decrease statistically. However, in some persons, when they feel sleepiness, any intentional motion of an eyelid to bear the sleepiness, such as opening eyes wide intentionally, blinking vigorously, could be made, and thus, in the cases of such subjects, the value and/or variation of "the time interval between the transition between the opened state and closed state of the eyelid" increase. Thus, in the above-mentioned inventive device, an upper threshold value and a lower threshold value lower than the upper threshold value may be set and the sleepiness judging device may be designed to judge that the subject feels sleepiness when the eyelid opening/closing characteristic amount deviates from the range between the upper threshold value and lower threshold value. Further, in setting the threshold values with eyelid opening/closing characteristic amounts obtained in a predetermined period, as one manner, as explained in embodiments described later, values obtained by multiplying a predetermined positive number smaller than 1 or a predetermined positive number larger than 1 to an average value of eyelid opening/closing characteristic amounts obtained in a predetermined period may be set for the lower threshold value and the upper threshold value, respectively.

With respect to the above-mentioned judgment of the presence or absence of sleepiness, as already noted, there are individual variations and intraindividual variations in the time intervals between transitions between the opened state and closed state of an eyelid in either cases when a subject feels no sleepiness and when a subject feels sleepiness. Accordingly, preferably, the threshold values to be used for the references in judging the presence or absence of sleepiness for a certain subject are determined with time intervals between transitions between the opened state and closed state of an eyelid of the certain subject in the period relatively close to the time of conducting the judgment of sleepiness. In this respect, in a case of an in-vehicle sleepiness detecting device for detecting sleepiness of a subject driving a vehicle, it is assumed that the driver (subject) does not feel sleepiness just after the starting of driving the vehicle, and thus, typically, the threshold values will be set using eyelid opening/closing characteristic amounts obtained in a predetermined period from the starting of running the vehicle, for example, a period until statistically significant data volume is obtained. On the other hand, when the driving is interrupted, such as for taking a break during driving a vehicle, there is a case that the condition of the driver after the interruption of the driving has changed at a degree that it is better to execute the resetting of threshold values, while there is also a case that no such changes occur and thus the resetting of threshold values is not necessary. Then, in the present invention, as noted above, the threshold value setter is configured to judge, at the restarting of driving the vehicle after its interruption, whether the resetting of threshold values is to be performed based on the condition of the subject before the restarting of the driving, and to reset the threshold values using eyelid opening/closing characteristic amounts obtained in a predetermined period after the restarting of the driving when it is judged that the resetting of threshold values is to be performed. According to this structure, it can be avoided that, in spite that the resetting of threshold values is unnecessary, the resetting of threshold values would be performed so that the detection of sleepiness could not be performed in a period taken for the setting.

With respect to the judgment of whether to perform the resetting of threshold values, more concretely, in one manner, since the possibility that the subject's condition changes becomes higher when the time length of an interruption of the driving is longer, the resetting of threshold values may be performed when the time length of an interruption of the driving a vehicle is longer than a predetermined time. The length of the predetermined time may be set experimentally. Further, in another manner, when sleepiness of the subject is detected before an interruption of driving a vehicle, the resetting of threshold values may be performed. For example, in a case that driving a vehicle is interrupted for taking a break because a driver feels sleepiness during the driving, the manner of the variation of the eyelid opening/closing characteristic amount in a normal condition can change from the condition before the interruption of the driving. In that case, if the same threshold values as in the condition before the interruption of the driving are used continuously, an erroneous judgment of the presence or absence of sleepiness becomes likely to occur, and thus, the resetting of threshold values may be performed. In this regard, when either one of the above-mentioned conditions is established, the resetting of threshold values may be performed.

Furthermore, the above-mentioned structure may be designed such that, until the threshold value setter completes the setting of threshold values with the eyelid opening/closing characteristic amounts obtained in the predetermined period, the sleepiness judging device judges whether or not the subject feels sleepiness, using threshold values being set with time series data of time intervals between transitions between the opened state and closed state of the eyelid obtained before the predetermined period. For example, when a driver (a subject) drives a vehicle for the first time in one day, no data of eyelid opening/closing characteristic amounts of the driver in that day have been obtained, and thus, in that case, threshold values obtained using the data obtained in the days before the present day may be used. In this case, in order to improve the statistical reliability of the threshold values to be set, the data over two or more days (relatively close to the present day) may be used. In this respect, since it has been found that a driver is more likely to feel sleepiness during running on a highway road than during running on an ordinary road, it is preferable to use the data obtained during running on an ordinary road in the setting of threshold values.

By the way, as understood with reference to examples of eyelid opening/closing characteristic amounts in an embodiment described later, since the eyelid opening/closing characteristic amount can be a rather fluctuating value, the value can deviate momentarily from the range defined with the threshold values even in a normal condition. On the other hand, when a subject really feels sleepiness, its eyelid opening/closing characteristic amount will repeatingly or continuously deviates from the range defined with the threshold values. Then, in order to avoid making an erroneous judgment of an occurrence of sleepiness due to momentary fluctuation in the eyelid opening/closing characteristic amount, in the inventive device, the sleepiness judging device may be configured to judge that the subject feels sleepiness when a time length in which the eyelid opening/closing characteristic amount has deviated from the range defined with the threshold values exceeds beyond a predetermined length or when a number of times that the eyelid opening/closing characteristic amount deviates from the range defined with the threshold values exceeds beyond a predetermined number of times.

Moreover, in the above-mentioned inventive device, the threshold value setter may be configured to set a plurality of threshold values having mutually different magnitudes, and the sleepiness judging device judges which stage a degree of the sleepiness of the subject falls into among two or more stages based on relationships in magnitude of the eyelid opening/closing characteristic amount to the respective plural threshold values. The eyelid opening/closing characteristic amount deviates from the range defined with the threshold values more largely as the degree of sleepiness is stronger. Thus, by setting two or more stages in the ranges defined with the threshold values and judging which stage the eyelid opening/closing characteristic amount reaches, it becomes possible to judge the degree or the strength of sleepiness.

Effect of Invention

Thus, in a case of detecting sleepiness of a driver (a subject) during driving a vehicle in the above-mentioned inventive structure, when the driver makes an interruption of the driving in which any change in the condition of the subject can occur, it will be determined whether to carry out the resetting of threshold values based on the situation until the restarting of the driving, and thus, it becomes possible to conduct the detecting of sleepiness accurately also after the restarting of the driving, and together with this, it can be avoided to carry out unnecessary resetting of threshold values. According to this structure, a blank time when no detection of sleepiness is performed can be shortened as much as possible, and since the time in which the process of detection sleepiness is available becomes longer, the detection of sleepiness of a driver during driving a vehicle can be more certainly performed.

Other purposes and advantages of the present inventions will become clear by explanations of the following preferable embodiments of the present invention.

BRIEF DESCRIPTIONS OF DRAWINGS

Figure 1B:
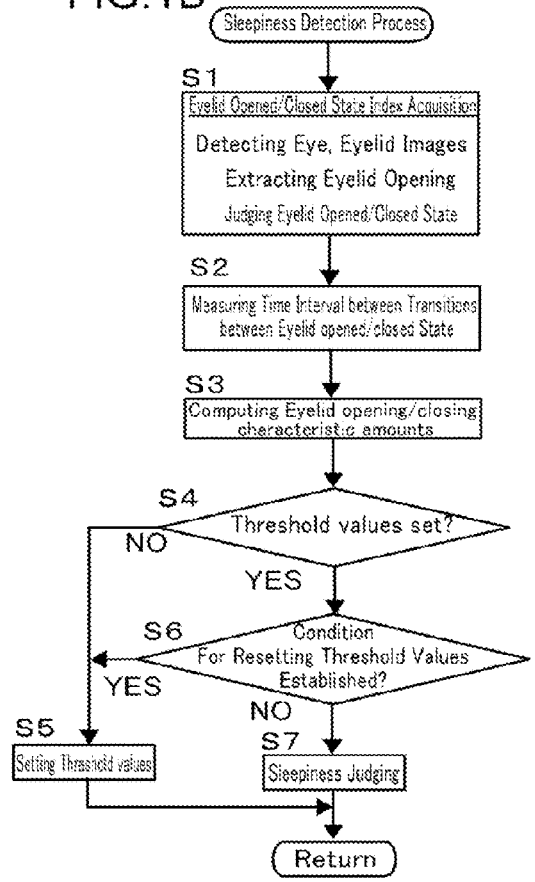

FIG. 1A schematically shows the structure of an embodiment of a sleepiness detecting device according to the present invention, and FIG. 1B shows an overview of the operations of the embodiment of the sleepiness detecting device according to the present invention in the form of a flow chart.

FIG. 2 A shows a schematic diagram of a subject's face in capturing an image of an eye and an eyelid with a camera in the inventive sleepiness detecting device. FIG. 2B shows an example of a time variation of an opening of an eyelid obtained from images of the eyelid, and an example of a time variation in the eyelid opened/closed state index value obtained by binarizing the opening of the eyelid. FIG. 2C shows schematically an arrangement of electrodes attached to a subject's face, when the opening of an eyelid is detected with an ocular potential signal in the inventive sleepiness detecting device.

Figure 3A:
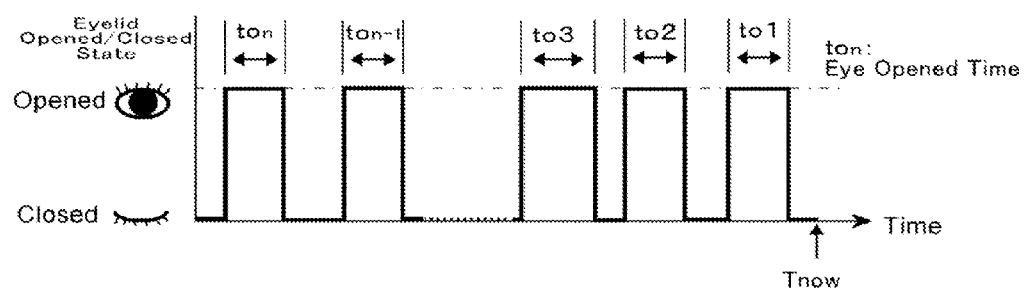
Figure 3B:
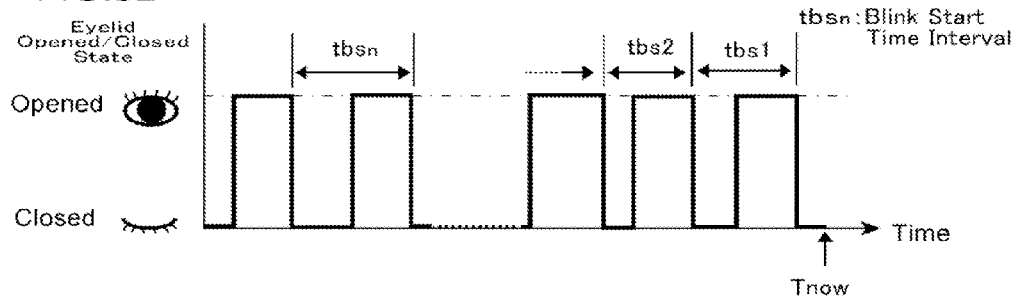
Figure 3C:
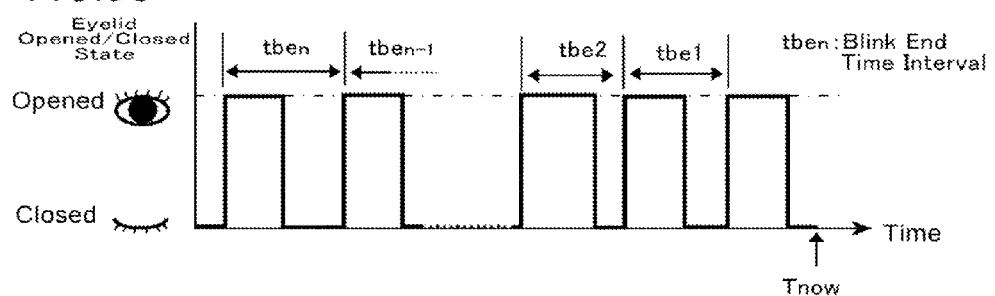

FIG. 3A is a drawing explaining about an "eye opened time" measured in time series data of eyelid opened/closed state index value. FIG. 3B is a drawing explaining about a "blink start interval" measured in time series data of eyelid opened/closed state index value. FIG. 3C is a drawing explaining about a "blink end interval" measured in time series data of eyelid opened/closed state index value.

Figure 4A:
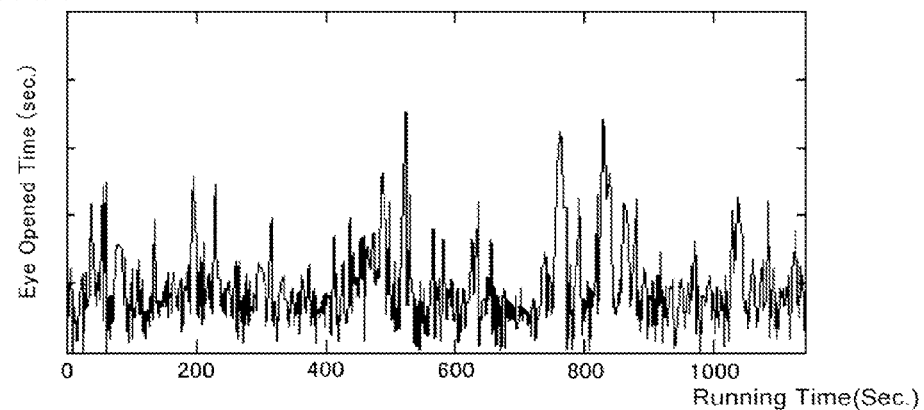
Figure 4B:
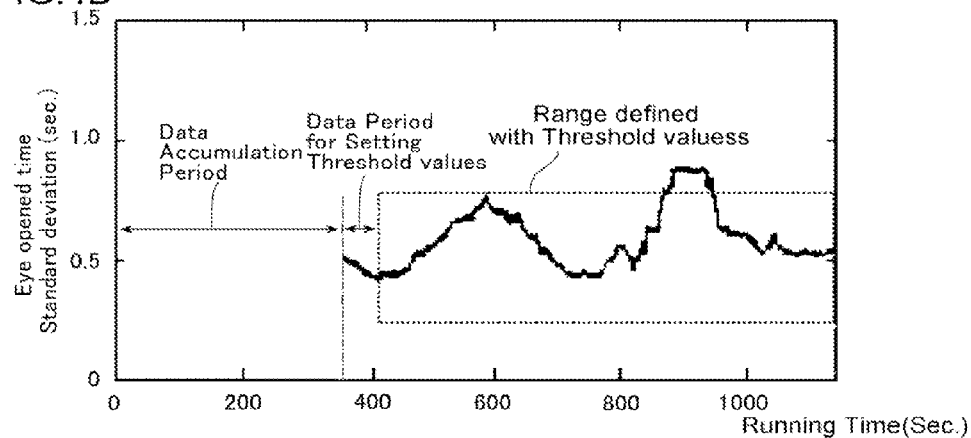

FIG. 4A shows an example of time series data of eye opened time, measured in eyelid opened/closed state index values obtained from time variation of the opening of an eyelid obtained from images of an eye and an eyelid. FIG. 4B shows time series data of standard deviation of eye opened time computed as the eyelid opening/closing characteristic amount from the time series data of the eye opened time of FIG. 4A. FIG. 4 C shows the time series data of standard deviation of eye opened time computed after removing noises (data of large values and data of small values) in the time series data of the eye opened time of FIG. 4A.

Figure 5A:
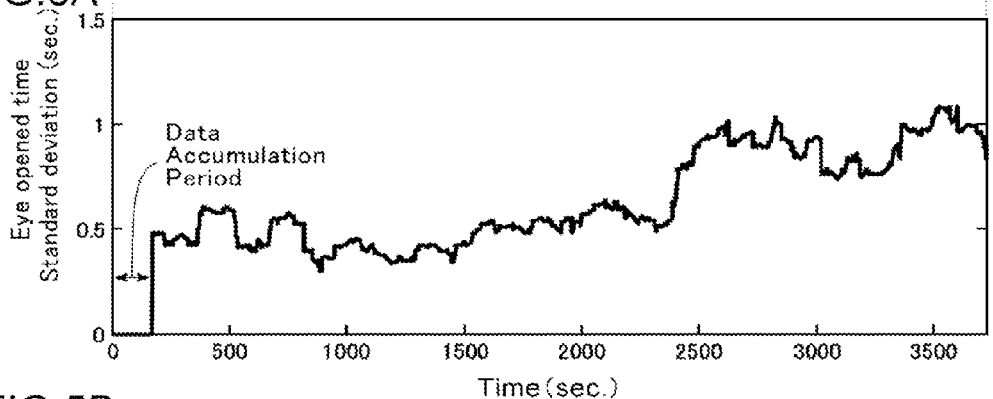
Figure 5B:
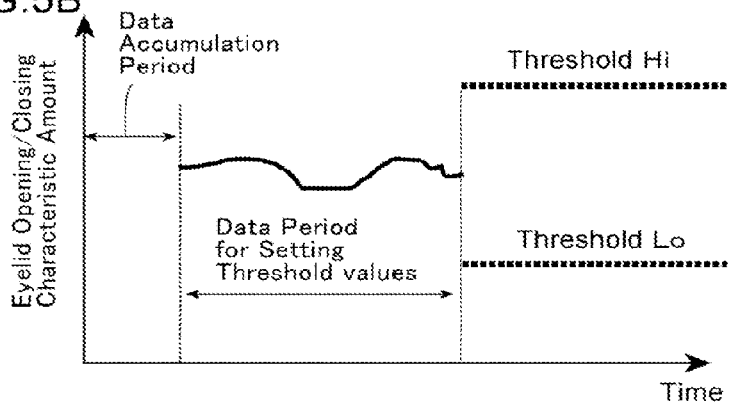

FIG. 5A shows an example of time series data of standard deviation of eye opened time computed from time series data of eye opened time, and FIG. 5B is a drawing explaining about a method of setting threshold values for eyelid opening/closing characteristic amount in time series data of eyelid opening/closing characteristic amount as in FIG. 5A. FIG. 5 C shows an example of a set of threshold values set for two or more stages in determining the degree of sleepiness.

Figure 6A:
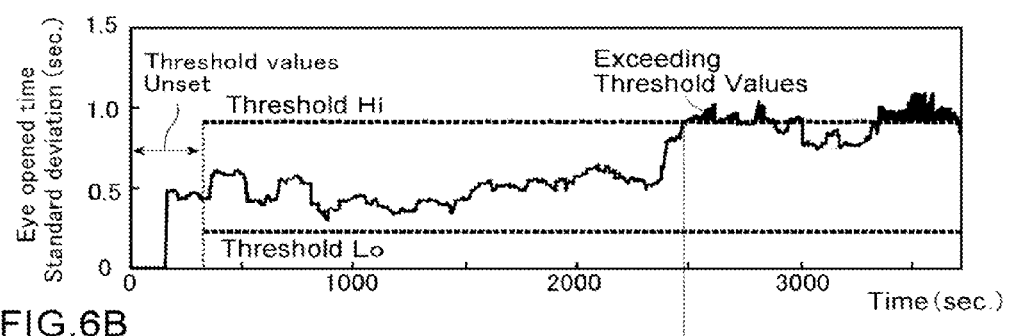
Figure 6B:
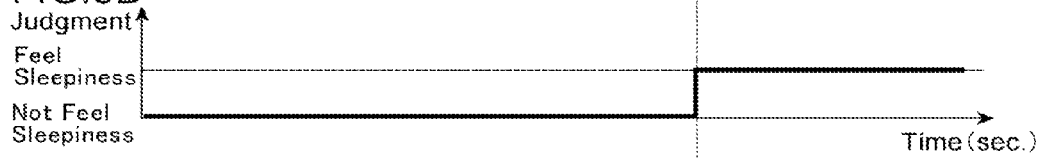
Figure 6C:
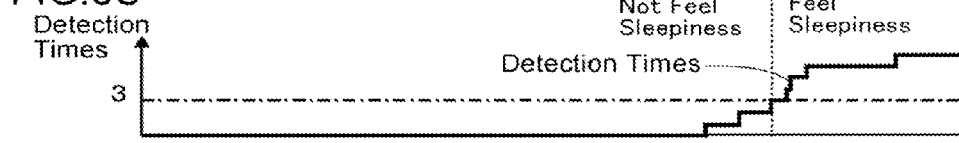
Figure 6D:
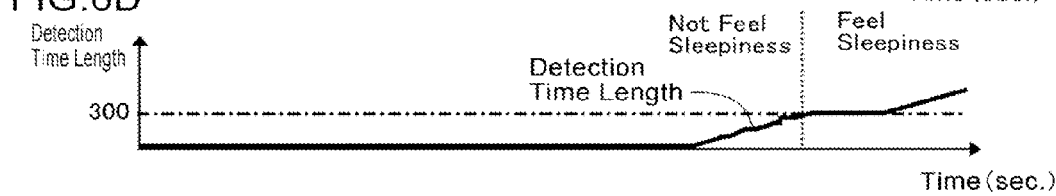

FIG. 6A shows time series data of standard deviation of eye opened time (eyelid opening/closing characteristic amount) computed from time series data of eye opened time obtained from eyelid images and threshold values having been set. FIG. 6B is a drawing explaining about a case of making the judgment of an occurrence of sleepiness when the eyelid opening/closing characteristic amount deviates from the range defined with threshold values one time in the data of FIG. 6A; FIG. 6C is a drawing explaining about a case of making the judgment of an occurrence of sleepiness when the eyelid opening/closing characteristic amount deviates from the range defined with threshold values a predetermined times (three times in the illustrated example) in the data of FIG. 6 A; and FIG. 6D is a drawing explaining about a case of making the judgment of an occurrence of sleepiness when the length of time in which the eyelid opening/closing characteristic amount deviates from the range defined with threshold values reaches a predetermined time length (300 seconds in the illustrated example) in the data of FIG. 6A.

Figure 7A:
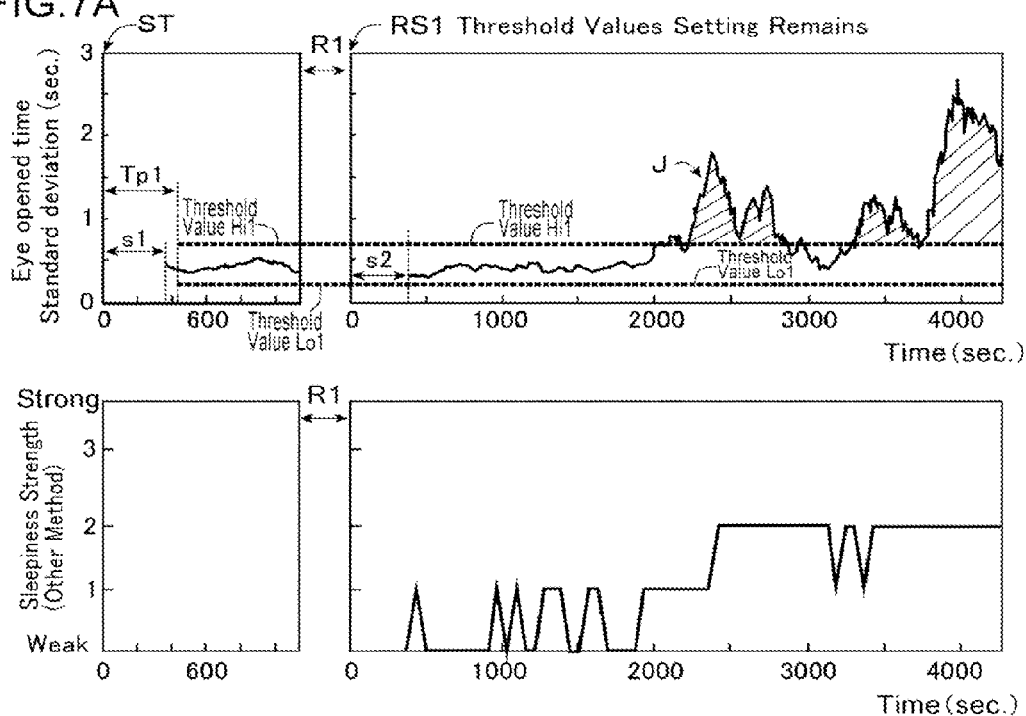
Figure 7B:
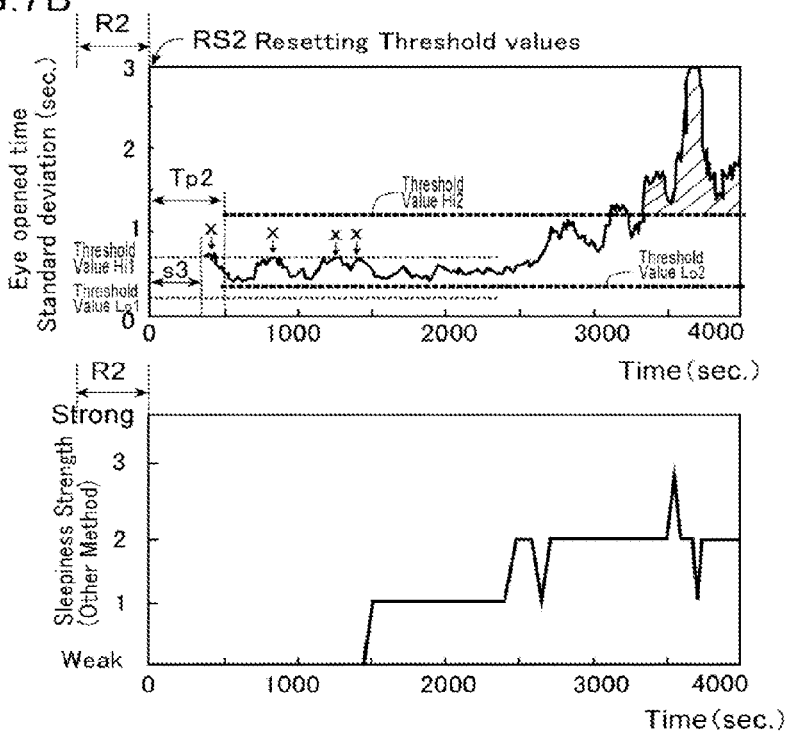

FIGS. 7A and 7B are time series data of standard deviation of eye opened time of a driver during driving a vehicle, indicating an example in which an interruption for a break has been made during the driving. In FIG. 7A, there occurred an interruption of driving for a break in R1, and in FIG. 7B, there occurred an interruption for a break in R2. The lower columns of FIGS. 7A and 7B show the strength of sleepiness of the driver measured by a different way (the method described in non-patent document 4) in the same driving.

FIG. 8 shows time series data of eye opened time during driving a vehicle before the present days for setting provisional threshold values in a period of collecting the data of eyelid opening/closing characteristic amounts for setting threshold values just after the starting of driving a vehicle.

EXPLANATIONS OF REFERENCE NUMERALS

1—Subject
2—Eye of a subject
3—Camera
4—Signal processing device

DESCRIPTION OF EMBODIMENTS

In the followings, preferable embodiments of the present invention are described in detail. In the drawings, the same numeral references indicate the same parts.

Structure of Device

Briefly, the sleepiness detecting device in accordance with the present invention is a device of a type which measures opening and closing motions of an eyelid of a subject, extracts eyelid opening/closing characteristic amounts having a correlation with the subject's sleepiness from time series data of the measured opening and closing motions of the eyelid, and judges that the subject feels sleepiness when the eyelid opening/closing characteristic amount deviates from a range in which the subject does not feel sleepiness, similarly to patent document 1, Japanese Patent Application No. 2015-25886, etc. Referring to FIG. 1A, in the basic structure of the inventive sleepiness detecting device, first, an image capturing device, such as a camera 3, is set so that an eye and an eyelid 2 of a subject 1 will be covered in the field of view of the image capturing device, and image signals acquired with the image capturing device are taken into a signal processing device 4. In this regard, as mentioned later, the opening and closing motion of the eye and eyelid 2 of the subject 1 may be detected with ocular potential signals, and in that case, the signals from electrodes applied on the subject's face are given to the signal processing device 4. Then, in the signal processing device 4, an image processing portion generates an image including the image of the eye and eyelid 2 of the subject 1 from the image signals sent from the image capturing device. And, using the images of the eye and eyelid 2 of the subject, a data processing portion performs data processing necessary for detection of sleepiness of the subject and a judgment of the presence or absence of sleepiness, as described later. Thus, when a judgement that the subject feels sleepiness is made in the data processing portion, the judgment result is transmitted to a result output portion, where, for instance, the result is informed to the subject through sound with a speaker 5, a physical stimulus given to the subject by a vibrator, etc. The signal processing devices 4 may be, typically, a computer device, equipped with a CPU, memories, input/output device (I/O), etc. mutually connected with bidirectional common bus (not illustrated) in a usual manner, and operations of the respective portions of the sleepiness detecting device are achieved by executing computer programs in CPU.

In this regard, in the inventive device, when an interruption of driving a vehicle occurs, a process of judging whether to perform the resetting of threshold values after the interruption. For this, in addition to the above-mentioned structures, information (vehicle driving condition information) for detecting whether the vehicle is being driven or not is inputted into the data processing portion of the signal processing device 4. For examples of vehicle driving condition information, there may be employed a signal indicating a vehicle speed, a signal indicating ON/OFF of a drive switch or an ignition switch, etc. In the data processing portion, it is judged with such a signal whether or not the vehicle is being driven, and with reference to this information, when there occurs an interruption of the driving, the time length from the interruption, etc. is measured until the driving is restarted, and as explained later, it will be determined with reference to the length of the time of the interruption, etc. whether the resetting of threshold values is to be performed.

Overview of Operations of Device

Referring to FIG. 1B, in the processes of detecting sleepiness by the inventive device, during driving a vehicle, according to the programs, first, the index value indicating the opened/closed state of an eyelid of a subject (a driver) is sequentially acquired (step 1), and, in the time series data of the index values, a time interval between transitions between the opened state and closed state of the eyelid is sequentially measured (step 2), and next, the "eyelid opening/closing characteristic amount" having a correlation with the presence or absence of sleepiness in the time series data of the time intervals between transitions between the opened state and closed state of the eyelid is sequentially computed (step 3). Then, when the threshold values for the "eyelid opening/closing characteristic amount" for the judgment of the presence or absence of sleepiness have not been set yet (usually, in a predetermined period from just after starting the use of the device), processes for the setting of the threshold values are executed (steps 4 and 5). Thus, when the threshold values have been set after the repeating of the cycle in a predetermined period as described later (step 4), the judgment of sleepiness of the subject will be conducted (step 7). Further, in a case of the in-vehicle sleepiness detecting device, when there occurs an interruption of the driving for taking a break, etc., there is a case that the resetting of the threshold values becomes necessary at the time of restarting of the driving, depending on the subject's condition. Then, in the present embodiment, after checking that the threshold values have been set (step 4), there is executed a process (step 6) of judging whether a condition that the resetting of threshold values is to be performed is established, and when it is judged that the condition that the resetting of threshold values is to be performed is established, more concretely, when it is judged that a condition that it is better to carry out the resetting of the threshold values as described later is established at the restarting of the driving after the interruption, a process for the setting of the threshold values (step 5) will be performed. In this regard, in the device of the present embodiment, the eyelid state detector, the time interval detector, the eyelid opening/closing characteristic amount computer, the threshold value setter and the sleepiness judging device each are realized by the image capturing device (or electrode device) in FIG. 1(A) and the operations of the signal processing device 4 according to the programs. In the followings, each process in the above-mentioned series is explained in detail.

Acquisition of Eyelid Opened/Closed State Index Value (Step 1)

In the acquisition of index values indicating opened/closed state of an eyelid of a subject (eyelid opened/closed state index value) in the inventive device, in one manner, as noted, the opening and closing motions of an eyelid are detected in images of an eye and an eyelid of a subject sequentially captured with an image capturing device such as a camera, and there is prepared time series data indicating a state that the eyelid is opened and a state that the eyelid is closed from the detected data of the opening and closing motions of the eyelid. In that case, first, the image capturing device, such as a camera etc. may be installed on an arbitrary place so that the field of view may cover the subject's eye and eyelid, as schematically drawn in FIG. 2A. For instance, in a case of judging sleepiness of a driver of a vehicle, a concrete position of an image capturing device, such as camera etc., may be set to an arbitrary place, as long as the image of the subject's eye and eyelid can be captured, such as on the dashboard of a vehicle, a handle, a ceiling, etc. Also, the image capturing device, such as a camera etc., may be attached to any subject's wearing article, such as glasses, a hat, etc. The image capturing device, such as a camera, etc., sequentially takes photographs of the subject's eye and eyelid and outputs image signals, from which the images of the eye and eyelid are formed sequentially.

When the successive or continuous images of the subject's eye and eyelid are obtained, the positions of an upper eyelid and a lower eyelid are sequentially detected in the images and the distances between the upper and lower eyelids are measured, and thereby, time series data of an opening of the eyelid (the distance between the upper and lower eyelids) is prepared as drawn in FIG. 2B, the upper row. The detection of the positions of an upper eyelid and a lower eyelid in an image may be done by an arbitrary image processing method based on properties in brightness or hue of images of the upper and lower eyelids or the image of an eyeball. And the obtained time series data of the opening of the eyelid is binarized into an opened state and a closed state by judging whether or not each data value exceeds beyond a threshold value which is set to the boundary of the opened state and the closed state of the eyelid between the maximum and the minimum of the eyelid opening, and thereby, there is prepared time series data of the eyelid opened/closed state index value, which is an index value indicating whether or not the eyelid is opened or closed, as drawn in FIG. 2B, the lower row.

The eyelid opening may be measured in any other manner, and it should be understood that such a case belongs to the scope of the present invention, also. Alternatively, as already noted, for example, the eyelid opening can be measured with the height of an ocular potential signal of a subject (voltage change owing to the rotation of the eyeball accompanying blinking). In that case, as schematically drawn in FIG. 2C, for example, plural electrodes each are applied on plural regions, such as the upper and lower sides of a subject's eye, and the voltage between the electrodes is measured as a signal (ocular potential signal), and transmitted to the signal processing device. Further, electrodes may be attached to any head wearing article, such as glasses, goggles, a helmet, or may be built in any accessory, such as a tattoo applied on skin. Also in the case of the ocular potential signal, time series data similar to that in FIG. 2B are obtained for the motions of an eyelid, and thus, by binarizing that data, time series data of eyelid opened/closed state index values will be prepared.

In this regard, as explained later, since calculation processes of a statistical quantity of the eyelid opened/closed state index value over a certain period is conducted in the process of the inventive device, the time series data of eyelid opened/closed state index values are memorized by the data memory in the signal processing device 4.

Computation of Eyelid Opening/Closing Characteristic Amount (Steps 2 and 3)

When time series data of eyelid opened/closed state index value is obtained, an amount which has a correlation with the presence or absence of sleepiness of a subject is extracted from the time series data of the eyelid opened/closed state index value. In the present invention, this amount which has a correlation with the presence or absence of the subject's sleepiness is referred to as an "eyelid opening/closing characteristic amount". In this embodiment, the "eyelid opening/closing characteristic amount" is computed out by measuring sequentially time intervals between transitions of the eyelid opened/closed state in the time series data of eyelid opened/closed state index value in a predetermined period and processing statistical calculations of the measured transition time intervals. In the followings, the computation process of the "eyelid opening/closing characteristic amount" is explained.

(i) Measurement of Time Interval Between Transitions of Eyelid Opened/Closed State (Step 2)

In the computation process of eyelid opening/closing characteristic amount, first, a time interval between transitions between the opened state and closed state of an eyelid is measured in time series data of eyelid opened/closed state index value memorized in data memory. As described in the column of "Summary of Invention", the time interval between transitions between the opened state and closed state of an eyelid (Hereinafter, referred to as "eyelid opened/closed state transition time interval") is the interval between time points of occurrences of transitions of an eyelid from the opened state to the closed state or from the closed state to the opened state. Concretely, the "eyelid opened/closed state transition time interval" may be: (1) Eye opened time (a time length in which an eyelid is continuously opened), i.e., a time interval from a transition of an eyelid from its closed state to its opened state to a transition of the eyelid from its opened state to its closed state (FIG. 3A); (2) Blink start time interval (a time length from when an eyelid is closed until it is closed again after it is once opened), i.e., a time interval from a transition of an eyelid from its opened state to its closed state to the next transition from its opened state to its closed state(FIG. 3B); (3) Blink end time interval (a time length from when an eyelid is opened until it is opened again after it is once closed), i.e. a time interval from a transition of an eyelid from its closed state to its opened state to the next transition of from its closed state to its opened state (FIG. 3 C); and (4) Eye closed time (a time length in which an eyelid is continuously closed), i.e., a time interval from a transition of an eyelid from its opened state to its closed state to a transition of the eyelid from its closed state to its opened state. Further, in either of the cases (1)-(4), the time series data of values of time intervals of transitions are prepared by measuring the eyelid opened/closed state transition time interval while tracing back to the past from the present (Tnow) as drawn in FIG. 3A-FIG. 3C. For example, in the case of eye opened time in FIG. 3A, time series data is constituted by measuring the eye opened times $to_1$, $to_n$ while tracing back from the present time Tnow as $to_1$, $to_2$, $to_3$, ..., $to_{n-1}$, $to_n$. FIG. 4A shows an example of time series data of eye opened time, measured in eyelid opened/closed state index values obtained from the time variation of the opening of an eyelid obtained from images of an eye and an eyelid.

(ii) Computation of Eyelid Opening/Closing Characteristic Amount (Step 3)

As noted above, when the eyelid opened/closed state transition time intervals have been measured, a statistic amount of the eyelid opened/closed state transition time intervals is computed as an eyelid opening/closing characteristic amount, using an arbitrary number of the data while tracing back along the time-axis from the present or judgment point. For the statistic amount, there may be employed the standard deviation value, the variance value, the average value, the median value, etc. Concretely, for example, in a case that the eye opened time is chosen as the eyelid opened/closed state transition time interval and the standard deviation value of the eye opened time is chosen as the eyelid opening/closing characteristic amount, while tracing back from the present time point, n points of eye opened time data:

$$\{to_1, to_2, to_3, to_{n-1}, to_n\} \quad (1)$$

are extracted from data memory, and the standard deviation value SD (t) is computed by $$SD(t) = \sqrt{\frac{1}{n}\sum_{i=1}^{n}(toi - toa)^2} \quad (2)$$

Here, n is the number of extracted data points; i is the data number, toi is the i-th eye opened time data, and toa is the average value of n points of the extracted data values. And the standard deviation value (eyelid opening/closing characteristic amount) SD (t) is sequentially computed as shown in FIG. 5A during repeating the cycle of FIG. 1B. In this regard, referring to the drawing, in a certain period from the start of the process (data accumulation period), since the number of data points has not reached to the number required for computing a statistically significant eyelid opening/closing characteristic amount, the eyelid opening/closing characteristic amount is not computed. It will be understood that, also in the cases of selecting the variance value, the average value or the median value of blink start time intervals, blink end time intervals or eye closed times for the eyelid opening/closing characteristic amount, similarly, the eyelid opening/closing characteristic amount is computed in time series with an arbitrary number of data while tracing back along the time-axis from the present time point or the judgment time point.

By the way, during driving a vehicle, when a driver gazes at an object to be noticed, such as another vehicle, a walker, a road sign, there is a case that the eye opened time takes a different value from usual, and thus, the standard deviation of the eye opened time can be changed also. Such a change cannot be distinguished from a change owing to an occurrence of sleepiness, causing an erroneous decision in the judgment of sleepiness as explained later. Then, in the present embodiment, a process for removing influences of changes of the eye opened time owing to the subject gazing at an object during driving a vehicle (referred to as "noise by gaze" hereafter.) may be performed. In this respect, while an occurrence of sleepiness is typically a phenomenon lasting in the order of several minutes to several hours, the gazing of an object to be noticed is a transient phenomenon for the object passing by, and therefore, a change of the eye opened time owing to this is also considered to be transient. Thus, taking into account that a noise owing to the gazing of an object to be noticed in the time series data of the eye opened time is transient, either process in the following manners is performed to time series data of eye opened time before the calculation of eyelid opening/closing characteristic amount for the process of removing noises.

In the first manner of the process of removing noises owing to the gazing, nh data points of the higher values and nl data points of the lower values are removed in the time series data of the eye opened time for computation of eyelid opening/closing characteristic amounts [m data points], and thereby, the computation of eyelid opening/closing characteristic amounts is performed with the remaining time series data of eye opened time[m−(nh+nl) data points]. In a concrete process, after acquisition of time series data of eye opened time, rearrangement of data is performed in accordance with the magnitudes of the values of the data, and the higher nh data points and the lower nl data points are removed in the data row. In this regard, the number of the data removed in this case may be changed.

In the second manner of the process of removing noises owing to the gazing, h % of both ends in the data distribution are removed from the time series data of the eye opened time for computation of eyelid opening/closing characteristic amounts [m data points], and thereby the computation of eyelid opening/closing characteristic amounts is performed with the remaining time series data of eye opened time. In a concrete process, after acquisition of time series data of eye opened time, rearrangement of data is performed in accordance with the magnitudes of the values of the data, and in both the higher and lower side in the data low, m×h/100 data points are removed, respectively.

Figure 4C:
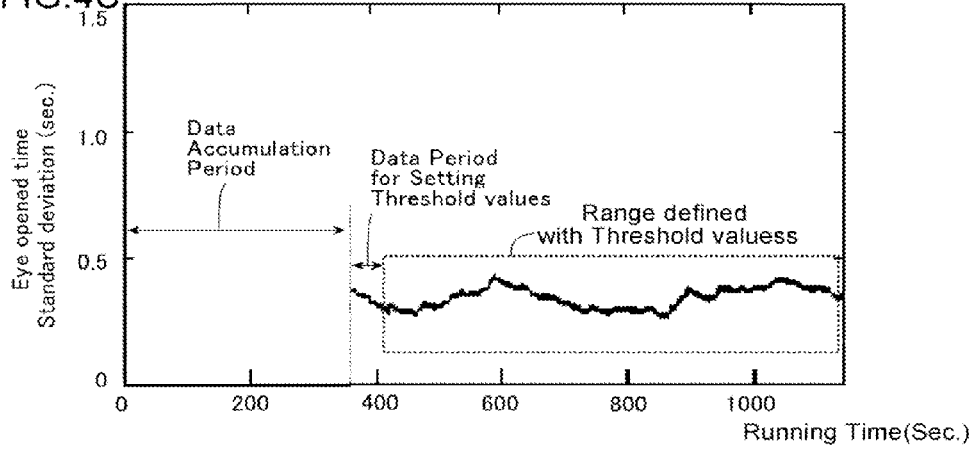

FIGS. 4B and 4C each are examples of time series data of standard deviation of eye opened time of a subject during driving a vehicle, where FIG. 4B shows the standard deviation of eye opened time computed without performing the above-mentioned noise removal while FIG. 4C shows the standard deviation of eye opened time computed after performing noise removal in the above-mentioned first manner. With reference to those drawings, although the driver does not feel sleepiness in the illustrated data, the standard deviation of eye opened time computed without performing noise removal in FIG. 4B had a rather large variation and there occurred cases that the standard deviation temporarily deviates from the range defined with threshold values. On the other hand, the variation of the standard deviation of eye opened time computed after performing noise removal in FIG. 4C was relatively small, and no deviation of the standard deviation from the range defined with threshold values was observed. Thus, by performing the process of removal of noises owing to the gazing as described above, reduction of erroneous detection of sleepiness can be achieved.

Setting of Threshold Valued (Steps 4 and 5)

In the present invention, as already noted, when the above-mentioned eyelid opening/closing characteristic amount, such as the standard deviation value of eyelid opened/closed state transition time intervals, deviates from a range in which a subject does not feel sleepiness, a judgment that the subject feels sleepiness is made. Therefore, the setting of threshold values for defining the range of the eyelid opening/closing characteristic amount in which a subject does not feel sleepiness is performed. Especially, in the device of the present embodiment, for the threshold values corresponding to the boundaries of the range of the eyelid opening/closing characteristic amount when a subject does not feel sleepiness, two threshold values, i.e., the lower limit threshold value and the upper limit threshold value are set, and thus, sleepiness becomes detectable in both of subjects whose eyelid opening/closing characteristic amount decreases and subjects whose eyelid opening/closing characteristic amount increases when they feel sleepiness as compared with when they do not feel sleepiness. Further, as noted, since there are individual variations and intraindividual variations of the range of the eyelid opening/closing characteristic amount when a subject does not feel sleepiness, it is preferable that the threshold values defining the range are set up based upon the eyelid opening/closing characteristic amounts when the subject does not feel sleepiness in a period as close to the time of judging sleepiness as possible. Then, in this embodiment, as schematically drawn in FIG. 5B, the threshold values may be set using the eyelid opening/closing characteristic amounts in a predetermined period just after the operation start of the inventive device. In particular, in a case of using the inventive device for judging sleepiness of a driver (a subject) of a vehicle, the period for accumulating data for the setting of threshold values may be a predetermined period just after the starting of running the vehicle (The judgment of sleepiness is carried out under the condition that the threshold values have been set after the lapse of the data period for setting the threshold values as illustrated).

In one manner of concrete processes for the setting of threshold values, the threshold value Hi (upper limit) and the threshold value Lo (lower limit) may be computed, using M of eyelid opening/closing characteristic amount data in a period for accumulating data for setting the threshold values by:

$$\text{Threshold value Hi} = Thh \times Mav \tag{3a}$$

$$\text{Threshold value Lo} = Thl \times Mav \tag{3b}$$

Here, Thh is a positive coefficient larger than one, and Thl is a positive coefficient smaller than one. Mav is the average value of M data points of the eyelid opening/closing characteristic amount. M, Thh, and Thl may be determined experimentally. According to the expressions (3a) and (3b), since the threshold values will be set with the average value of the M of eyelid opening/closing characteristic amounts of the same subject in the data period for setting threshold values in a period relatively close to the time of a judgment, it is expected that influences of individual variations or intraindividual variations in eyelid opening/closing characteristic amounts can be suppressed.

In the process cycle of the device, after computing an eyelid opening/closing characteristic amount (step 3), when threshold values has not been set (step 4), the process of setting threshold values is performed (step 5). In this process, a cycle is repeated until M of eyelid opening/closing characteristic amounts have been accumulated, and when the number of eyelid opening/closing characteristic amounts reaches to M, the upper and lower threshold values are computed and set with the above-mentioned expressions.

In this regard, the above-mentioned threshold values may be changed according to the situation during driving. For example, in a case of driving on a highway road, in a case of driving a vehicle for a long time, in a case of driving on the day next to a day that prolonged continuous driving had been performed, etc., since a driver is likely to feel sleepiness, the width of the range defined with the threshold values may be made narrower by reducing the coefficient Thh of the upper threshold value and increasing the coefficient Thl of the lower threshold value, so that it becomes possible to detect sleepiness more sensitively.

Figure 5C:
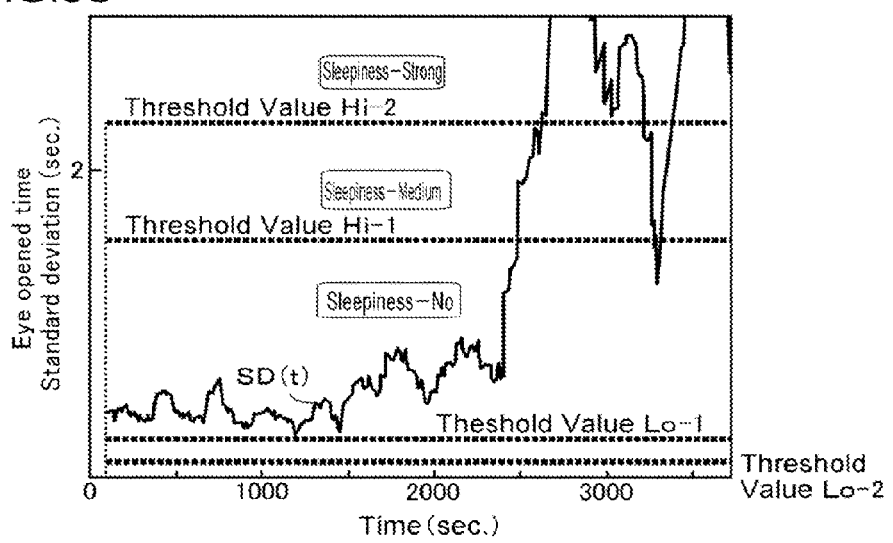

Moreover, typically, the eyelid opening/closing characteristic amount changes more largely from a normal condition as the degree of sleepiness becomes stronger. Thus, it is also possible to estimate the degree of sleepiness by referring to the width of change of eyelid opening/closing characteristic amount from the normal condition. Then, in the above-mentioned process of setting threshold values, a plurality of threshold values having mutually different magnitudes may be set so that plural stages will be set in the range defined with the threshold values. And in a case of the judgment of sleepiness mentioned below, it may be judged which stage the degree of sleepiness of the subject falls into among two or more stages based on the relationships in magnitude of the eyelid opening/closing characteristic amount to the respective plural threshold values. FIG. 5C shows an example in which two stages are set in the range defined with threshold values, and as illustrated, when the standard deviation (eyelid opening/closing characteristic amount) of eye opened time exceeds beyond threshold value Hi-1, the degree of sleepiness is judged to be in the stage of the medium degree, and when the standard deviation (eyelid opening/closing characteristic amount) of eye opened time exceeds beyond threshold value Hi-2, the degree of sleepiness is judged to be in the stage of the strong degree. According to this structure, it becomes possible to change the intensity of an alarm, etc. in order to caution a driver against the danger of napping step by step according to the strength of sleepiness, and accordingly, it becomes possible to notify that he/she is starting napping. In this regard, more than two stages may be set up in the range defined with threshold values.

Judgment of the Presence or Absence of Sleepiness (Step 7)

Then, when the threshold values have been set up (unless any condition of the resetting of threshold values is established), the judgment of whether or not the eyelid opening/closing characteristic amount is within the range defined between the upper and lower threshold values is conducted, and when the eyelid opening/closing characteristic amount deviates from the range between the upper and lower threshold values, it is judged that the subject feels sleepiness. FIG. 6A shows an example of conducting a judgment of sleepiness in time series data of standard deviation of eye opened time computed from time series data of eye opened time obtained from eyelid images (In the illustrated example, the threshold values were computed by setting M=100, Thh=2.0, and Thl=0.5.), and in this illustrated example, because the standard deviation exceeded beyond the threshold value Hi around 2500 seconds, it may be judged that a subject feels sleepiness, namely, "Feel Sleepiness" as shown in FIG. 6B.

However, as understood from the illustrated example, the eyelid opening/closing characteristic amount, as the standard deviation of the eye opened time, is highly fluctuating, which can deviate from the range defined with the threshold values momentarily even in a normal condition. On the other hand, as already described in conjunction with the explanations of the process of removing noises owing to the gazing, when a subject comes to truly feel sleepiness, the eyelid opening/closing characteristic amount becomes continuously or repeatedly deviating from the range defined with the threshold values. Then, in order to avoid erroneously judging an occurrence of sleepiness due to momentary fluctuations of the eyelid opening/closing characteristic amount, it may be designed to judge "Feel Sleepiness" after the eyelid opening/closing characteristic amount has become deviating from the range defined with the threshold values continuously at a certain degree. Concretely, in one manner, as shown in FIG. 6C, it may be designed to judge "Feel Sleepiness" when a number of times that the eyelid opening/closing characteristic amount deviates from the range defined with the threshold values exceeds beyond a predetermined number of times. Further, in another manner, as shown in FIG. 6D, it may be designed to judge "Feel Sleepiness" when the time length (integrated time) in which the eyelid opening/closing characteristic amount has deviated from the range defined with the threshold values exceeds beyond a predetermined length (in the illustrated example, 300 seconds). According to this structure, the judgment of an occurrence of sleepiness will be made in a situation that the accuracy of an occurrence of sleepiness becomes high, and thus, the risk of generating a false decision is reduced, and thereby, it is expected that the reliability of the sleepiness detecting device is increased.

Then, as noted above, when the sleepiness of the subject is detected, this may be informed to the subject with a loudspeaker or a vibrator, etc.

Resetting of Threshold Values (Step 6)

As noted, during driving a vehicle, there is a case that the driving is interrupted because of taking a break (a rest), etc. The time length of such an interruption can be about several minutes and also can reach 2 to 3 hours. And, it has been found out that the condition of the eyelid motion of the driver, i.e. the subject, can change before and after the interruption of the driving.

For example, with reference to FIGS. 7A and 7B, the illustrated example shows time series data of eyelid opening/closing characteristic amount (eye opened time standard deviation) in a case that there occurred an interruption of the driving for a break of about 10 minutes in R1 of FIG. 7A and an interruption of the driving for a break of about 60 minutes in R2 from the right end of FIG. 7A to the left end of FIG. 7B. In this regard, in the drawings, s1, s2, and s3 each are a time of accumulating the data of eye opened time for computing eyelid opening/closing characteristic amounts, and Tp1 and Tp2 each are a time width required to be taken for the setting of threshold values. Further, threshold value Hi1 and threshold value Lo1 are threshold values determined using eyelid opening/closing characteristic amounts just after the staring of the driving ST, and threshold value Hi2 and threshold value Lo2 are threshold values determined using eyelid opening/closing characteristic amounts just after the restarting of the driving RS2. As understood with reference to the eyelid opening/closing characteristic amounts in the drawings, it is observed that, for a certain period from just after the restarting of the driving RS1 after the first break R1, the variation of eyelid opening/closing characteristic amount therein is approximately similar to the variation of the eyelid opening/closing characteristic amount after the starting of the driving ST before the interruption. On the other hand, the variation of the eyelid opening/closing characteristic amount in the period from just after the restarting of the driving RS2 after the second break R2 for about 60 minutes exhibits larger fluctuation, differently from the variations of the eyelid opening/closing characteristic amount in the period just after the starting of the driving ST before the first interruption and in the period RS1 before the 2nd interruption (In this regard, it has been confirmed by a measurement of sleepiness strength in accordance with another method (the method described in Non-patent document 1) as shown in the lower column) that the driver did not feel sleepiness just after RS2.). Thus, if the threshold value Hi1 and threshold value Lo1, determined using the eyelid opening/closing characteristic amounts just after the staring of the driving ST are used continuously, the eyelid opening/closing characteristic amount would deviate from the range defined with the threshold values as indicated with "x" in the drawing, so that an erroneous judgment of "Feel Sleepiness" could be made in spite that the driver did not feel sleepiness. Therefore, it can be understood that it is necessary to carry out the resetting of threshold value Hi2 and threshold value Lo2 for the period RS2 just after the restarting of the driving using the eyelid opening/closing characteristic amount obtained therein. On the other hand, since changes in the variation of eyelid opening/closing characteristic amount are rarely observed just after the restarting of the driving RS1, it is preferable that the setting of threshold values requiring time(for example, Tp1, Tp2) is not performed.

Then, as already noted, in the present embodiment, it is judged whether or not there occurred an interruption of the driving which requires the resetting of threshold values, namely, whether or not any condition for the resetting of threshold values has been established, and when a condition for the resetting of threshold values has been established, the resetting of threshold values is performed as noted above. For example, the conditions for the resetting of threshold values may be as follows:

(a) A case that a judgment of an occurrence of sleepiness has been made before an interruption of the driving:
When a break is taken because a driver has felt sleepiness during the driving, the driver may take a napping, eating and drinking during the break for eliminating the sleepiness. Since there is a case that the eyelid opening/closing characteristic amount in a normal condition is changed by such an action for eliminating sleepiness after feeling sleepiness, it is preferable to execute the resetting of threshold values.
(b) A case that the time length of an interruption of the driving is longer than a predetermined time length:
Also in a prolonged interruption of driving, the driver takes a long rest, so that the eyelid opening/closing characteristic amount in a normal condition can change. Thus, also in that case, it is preferable to execute the resetting of threshold values.

Referring to the flow chart of FIG. 1 (B) again, in the cycle of the processes in the device, when the driving of a vehicle is interrupted and then restarted, after computing an eyelid opening/closing characteristic amount by executing the above-mentioned steps 1-3 and judging if the threshold values have been set (step 4), it is judged whether or not any condition for the resetting of threshold values is established, for example, whether or not either of the above-mentioned conditions (a) and (b) is established with reference to vehicle driving status information and the presence or absence of the judgement of "Feel Sleepiness" before the interruption of the driving. Then, when it is judged that no conditions for the resetting of threshold values are established, the judgment of sleepiness is performed (step 7) with the threshold values set before the interruption of the driving. On the other hand, when it is judged that at least one of the conditions for the resetting of threshold values is established, the process of setting threshold values is performed (step 5). Then, after the completion of the resetting of threshold values, the judgment of sleepiness is performed (step 7). In this regard, for the condition for the resetting of threshold values, there may be employed any other arbitrary conditions, in which it is considered that the eyelid opening/closing characteristic amount in a normal condition can be changed (e.g., change of the weather, brightness and time zone, etc.), and it should be understood that such a case belongs to the scope of the present invention.

Judgment of Sleepiness During Setting Threshold Values

By the way, the setting of threshold values takes a certain length of time (typically about several minutes) from the staring of driving a vehicle as noted above, and during this setting, the judgment of sleepiness would not be performed. In this respect, in the case of the sleepiness detecting device according to the present embodiment, except the resetting of threshold values during the driving as noted, the setting of threshold values is typically performed using the data of a predetermined period just after the starting of the first driving in a day in which the process of detecting sleepiness is performed. However, there is a case that, although a driver feels no sleepiness before the staring of the driving, sleepiness arises just after the staring of the driving because of any reason, such as poor physical condition, fatigue, etc. of the driver, and thus, it is preferable that the detection of sleepiness can also be performed from just after the starting of the driving.

Then, in the device of the present embodiment, until new threshold values have been set by the threshold value setting process (step 5), the process (step 7) of detecting sleepiness may be performed with threshold values set based on the eyelid opening/closing characteristic amounts computed using the data of eyelid opened/closed state index value in the past. For the data of eyelid opened/closed state index value in the past, typically, there may be preferably employed the time series data of eyelid opened/closed state index value measured during the running on an ordinary road in a period from the previous day of the day (the present day) when the process of detecting sleepiness is performed to several days ago, and typically, in a period from one day ago to three days ago. The reason for using the data from the previous day of the present day to several days ago as the time series data of eyelid opened/closed state index value to be used is in that, although it is preferable that the range of the data to used is as wide as possible in order to improve statistical reliability of threshold values to be set, there is a possibility that the condition of a subject could change largely if the day when the data were acquired separates from the present day too long, and if such data are contained in the data for computing threshold values, there is a possibility that the computed threshold values could not suit the subject's condition in the present day. Further, the reason for using the data measured during running on an ordinary road as the time series data of the eyelid opened/closed state index value is in that, typically, a possibility of occurrence of sleepiness during running on an ordinary road is lower as compared with during running on a highway road.

With reference to the flow chart of FIG. 1B again, in the cycle of the processes in the device, when it is judged in step 4 that the setting of threshold values is not completed, the judging of sleepiness in step 7 may be performed using threshold values determined using the data of eyelid opened/closed state index value in the past. In the setting of threshold values in this case, as illustrated in FIG. 8, using all the time series data of eyelid opened/closed state index value (the eye opened time in the illustrated example) acquired from one day ago to three days ago from the present day, except the data during running on a highway road, the time series data of eyelid opening/closing characteristic amount (for example, eye opened time standard deviation SD (ti), etc.) are computed similarly to the manner explained in conjunction with step 3 and step 5, and further, their average value Mav may be computed and threshold values Hi and Lo may be determined. In this regard, the coefficients Thh, Thl for computing the threshold values with the average value Mav may be different values from the case where the threshold values are computed using the data of the present day (For example, in order to reduce the sensitivity, the coefficient Thh, Thl may be set so that the width of the range defined with threshold values may become larger than that of threshold values based on the data in the present day.). Those threshold values may be computed beforehand at the time of the end of driving a vehicle in the previous day, or may be computed after the judgment of the above-mentioned step 4. The data of eyelid opened/closed state index value and/or threshold value data until the previous day may be stored in an arbitrary manner, and for example, may be stored in a memory device of an in-vehicle device, in a mobile phone or a memory of a server in a communication network.

Although the above explanation has been described with respect to embodiments of the present invention, it will be apparent for those skilled in the art that various modifications and changes are possible, and that the present invention is not limited to the above-illustrated embodiments and may be applied to various devices and apparatus without deviating from the concepts of the present invention.

The invention claimed is:

1. A device for detecting sleepiness of a subject driving a vehicle, comprising:
   an eyelid state detector which detects an opened/closed state of an eyelid of the subject;
   a time interval detector which detects sequentially a time interval between transitions between an opened state and a closed state of the eyelid;
   an eyelid opening/closing characteristic amount computer which computes an eyelid opening/closing characteristic amount successively from time series data of the time intervals between transitions between an opened state and a closed state of the eyelid,
   a threshold value setter which sets threshold values for the eyelid opening/closing characteristic amount using the eyelid opening/closing characteristic amount obtained in a predetermined period; and
   a sleepiness judging device which judges that the subject feels sleepiness when the eyelid opening/closing characteristic amount deviates from a range defined with the threshold values after lapse of the predetermined period;
   wherein the threshold value setter judges whether or not the threshold values are to be reset based on a condition of the subject before the restarting of the driving in restarting the driving of the vehicle after an interruption of the driving of the vehicle, and resets the threshold values for the eyelid opening/closing characteristic amount using eyelid opening/closing characteristic amounts obtained in the predetermined period after the restarting of the driving when it is judged that the threshold values are to be reset.

2. The device of claim 1, wherein the threshold value setter judges that the threshold values are to be reset when sleepiness of the subject is detected before the interruption of the driving of the vehicle.

3. The device of claim 1, wherein the threshold value setter judges that the threshold values are to be reset when a time length of the interruption of the driving of the vehicle is longer than a predetermined time length.

4. The device of claim 1, wherein, until the threshold value setter has completed the setting of the threshold values with the eyelid opening/closing characteristic amounts obtained in the predetermined period, the sleepiness judging device judges whether or not the subject feels sleepiness, using threshold values being set using time series data of time intervals between transitions between the opened state and closed state of the eyelid obtained before the predetermined period.

5. The device of claim 1, wherein the threshold value setter sets a plurality of threshold values having mutually different magnitudes, and the sleepiness judging device judges which stage a degree of the sleepiness of the subject falls into among two or more stages based on relationships in magnitude of the eyelid opening/closing characteristic amount to the respective plural threshold values.

6. The device of claim 1, wherein the sleepiness judging device judges that the subject feels sleepiness when a time length in which the eyelid opening/closing characteristic amount has deviated from the range defined with the threshold values exceeds beyond a predetermined length or when a number of times that the eyelid opening/closing characteristic amount deviates from the range defined with the threshold values exceeds beyond a predetermined number of times.

7. The device of claim 1, wherein the threshold value setter sets an upper threshold value and a lower threshold value lower than the upper threshold value, and the sleepiness judging device judges that the subject feels sleepiness when the eyelid opening/closing characteristic amount deviates from the range between the upper threshold value and the lower threshold value.

8. The device of claim 1, wherein the time interval between transitions between the opened state and the closed state of the eyelid is either of a time interval from a transition from the closed state to the opened state of the eyelid to a transition from the opened state to the closed state, a time interval from a transition from the opened state to the closed state to a next transition from the opened state to the closed state and a time interval from a transition from the closed state to the opened state to a next transition from the closed state to the opened state.

9. The device of claim 1, wherein the eyelid opening/closing characteristic amount is an index value representing a statistical change of the time intervals between the transitions between the opened state and the closed state of the eyelid.

10. The device of claim 9, wherein the eyelid opening/closing characteristic amount is a standard deviation of the time intervals between transitions between the opened state and a closed state of the eyelid.

11. The device of claim 1, wherein the threshold values are values obtained by multiplying a positive number smaller than one and a positive number larger than one to an average value of the eyelid opening/closing characteristic amounts obtained in the predetermined period, respectively.

12. The device of claim 1, wherein the eyelid state detector judges the opened/closed state of the eyelid based on a camera image of the eyelid or an ocular potential signal of the subject.

* * * * *